United States Patent
Marino

(10) Patent No.: US 9,192,396 B2
(45) Date of Patent: Nov. 24, 2015

(54) SYSTEM AND METHOD FOR ACCESSING BONE FOR CORING

(75) Inventor: James F. Marino, La Jolla, CA (US)

(73) Assignee: TRINITY ORTHOPEDICS, LLC, San Diego, CA (US)

(*) Notice: Subject to any disclaimer, the term of this patent is extended or adjusted under 35 U.S.C. 154(b) by 1249 days.

(21) Appl. No.: 11/861,232

(22) Filed: Sep. 25, 2007

(65) Prior Publication Data

US 2008/0077147 A1  Mar. 27, 2008

Related U.S. Application Data

(60) Provisional application No. 60/847,459, filed on Sep. 26, 2006.

(51) Int. Cl.
| | |
|---|---|
| *A61B 10/00* | (2006.01) |
| *A61B 17/00* | (2006.01) |
| *A61B 17/32* | (2006.01) |
| *A61B 17/16* | (2006.01) |
| *A61B 10/02* | (2006.01) |
| *A61B 17/3205* | (2006.01) |
| *A61B 17/34* | (2006.01) |

(52) U.S. Cl.
CPC ........... *A61B 17/1635* (2013.01); *A61B 10/025* (2013.01); *A61B 10/0266* (2013.01); *A61B 17/1633* (2013.01); *A61B 17/1671* (2013.01); *A61B 17/32053* (2013.01); *A61B 17/3472* (2013.01); *A61B 2010/0258* (2013.01)

(58) Field of Classification Search
CPC ............. A61B 10/025; A61B 10/0266; A61B 2010/025; A61B 2010/0258; A61B 17/1633; A61B 17/1635; A61B 17/1671; A61B 17/347; A61B 17/3472; A61B 17/32053

USPC .............. 600/562, 564, 567; 606/79, 80, 167, 606/170, 171, 172

See application file for complete search history.

(56) References Cited

U.S. PATENT DOCUMENTS

| | | | |
|---|---|---|---|
| 3,628,524 A * | 12/1971 | Jamshidi | ........................ 600/567 |
| 3,893,445 A | 7/1975 | Hofsess | |
| 4,789,547 A | 12/1988 | Song et al. | |
| 4,793,363 A * | 12/1988 | Ausherman et al. | .......... 600/567 |
| 5,040,542 A * | 8/1991 | Gray | .............................. 600/567 |
| 5,106,364 A | 4/1992 | Hayafuji et al. | |
| 5,341,816 A | 8/1994 | Allen | |
| 5,526,822 A | 6/1996 | Burbank et al. | |
| 5,649,547 A | 7/1997 | Ritchart et al. | |
| 5,730,752 A | 3/1998 | Alden et al. | |

(Continued)

*Primary Examiner* — Devin Henson
(74) *Attorney, Agent, or Firm* — Fred C. Hernandez; Mintz Levin Cohn Ferris Glovsky and Popeo, P.C.

(57) ABSTRACT

Disclosed is a bone coring device having a handle including a first handle component and a second handle component. The first handle component is rotatably coupled to the second handle component. The device also includes a coring assembly mechanically coupled to the handle. The coring assembly includes an elongated outer cutting member having an internal bore and distal edge adapted to cut through cancellous bone. The coring assembly also includes an elongated inner member slidably positioned within the internal bore of the outer cutting member. Rotatable movement of the first handle component relative to the second handle component causes relative, linear movement between the elongated outer cutting member and the inner member to facilitate coring of a sample of bone when the coring assembly is positioned within the bone.

19 Claims, 12 Drawing Sheets

Distal Direction

(56) References Cited

U.S. PATENT DOCUMENTS

| | | |
|---|---|---|
| 5,769,086 A | 6/1998 | Ritchart et al. |
| 5,807,277 A | 9/1998 | Swaim |
| 6,063,037 A * | 5/2000 | Mittermeier et al. .......... 600/567 |
| 6,248,081 B1 | 6/2001 | Nishtalas et al. |
| 6,554,778 B1 * | 4/2003 | Fleming, III ................. 600/567 |
| 7,033,324 B2 * | 4/2006 | Giusti et al. .................. 600/567 |
| 7,179,232 B2 * | 2/2007 | Sutton et al. ................. 600/567 |
| 2001/0005778 A1 | 6/2001 | Ouchi |
| 2001/0009978 A1 | 7/2001 | Krueger et al. |
| 2003/0229293 A1 | 12/2003 | Hibner et al. |
| 2005/0107800 A1 | 5/2005 | Frankel et al. |
| 2006/0247653 A1 * | 11/2006 | Akerfeldt et al. ............... 606/96 |
| 2007/0293788 A1 * | 12/2007 | Entrekin et al. .............. 600/564 |

\* cited by examiner

SYSTEM AND METHOD FOR ACCESSING BONE FOR CORING

REFERENCE TO PRIORITY DOCUMENT

This application claims priority of U.S. Provisional Patent Application Ser. No. 60/847,459 filed Sep. 26, 2006. Priority of the aforementioned filing date is hereby claimed and the disclosure of the Provisional Patent Application is hereby incorporated by reference in its entirety.

BACKGROUND

The present disclosure relates to devices and methods for coring an anatomical tissue. More particularly, the present disclosure relates to devices and methods for accessing and coring bone.

It is often necessary to access a core sample of biological material such as to diagnose defects or ailments. To obtain a sample, an instrument may be used to remove a portion or a "core sample" from surrounding biological material. In some circumstances, the cored material is bone. For example, it may be desirable for a physician to access cortical bone and then retrieve cancellous bone.

SUMMARY

There is a need for improved devices and methods for accessing and coring bone.

In one embodiment, there is disclosed a bone coring device having a handle including a first handle component and a second handle component, the first handle component being rotatably coupled to the second handle component; a coring assembly mechanically coupled to the handle, the coring assembly including an elongated outer cutting member having an internal bore and distal edge adapted to cut through cancellous bone; and an elongated inner member slidably positioned within the internal bore of the outer cutting member; such that rotatable movement of the first handle component relative to the second handle component causes relative, linear movement between the elongated outer cutting member and the inner member to facilitate coring of a sample of bone when the coring assembly is positioned within the bone.

Other features and advantages will be apparent from the following description of various embodiments, which illustrate, by way of example, the principles of the disclosed devices and methods.

DETAILED DESCRIPTION

Figure 1:
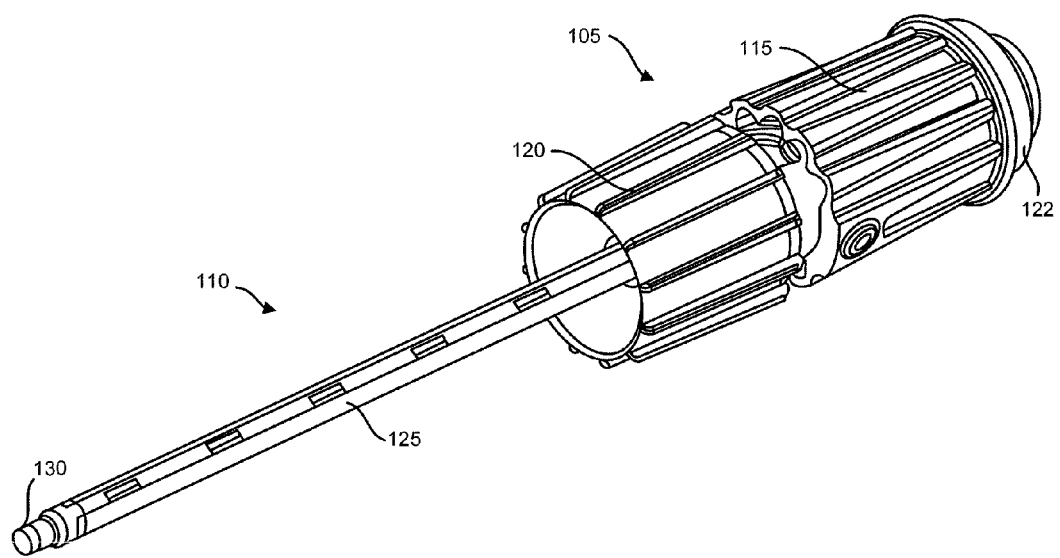
FIG. 1 shows a perspective view of a core sample device that is adapted to remove one or more core samples of bone tissue.

FIG. 1 shows a perspective view of a core sample device that is adapted to remove one or more core samples of tissue, such as bone tissue. The device includes a handle 105 that can be grasped by a user to hold and manipulate the device. The handle 105 is coupled to a cutting or coring assembly 110 that can be advanced into a material to be sampled, such as bone material, for retrieving a core sample of the material, as described in detail below. In an embodiment, the handle 105 serves as an actuator that is actuated to cause a first portion of the coring assembly 110 to move relative to a second portion of the coring assembly 110 to cut the material to be sampled. In this regard, the coring assembly 110 includes an outer cutting tube 125 and an inner tube 130 that is movably positioned concentrically within the outer cutting tube 125.

With reference still to FIG. 1, the handle 105 has a generally cylindrical shape that is adapted to fit within the hand of a user. As mentioned, the handle 105 can serve as an actuator that causes relative movement between components of the coring assembly 110. In this regard, the handle 105 includes a first handle component 115 and a second handle component 120 that is movably coupled to the first handle component 115. In an exemplary embodiment, the first handle component 115 is positioned at a proximal end of the device and the second handle component 120 is positioned distally of the first handle component 115. A cap 122 is positioned at a proximal-most region adjacent the first handle component 115. It should be appreciated that the relative positions of the first 115 and second 120 handle components can vary and that the shape of the handle 105 and its components can also vary, such as to provide ergonomic features.

The first handle component 115 (the proximal component) can be rotated relative to the second handle component 120 (the distal component) to cause relative movement between the outer cutting tube 125 and the inner tube 130 of the coring assembly 110. For example, rotational movement of the first handle component 115 relative to the second handle component 120 causes the inner tube 130 to linearly move or translate relative to the outer cutting tube 125, as described more fully below. In this regard, the inner tube 130 linearly translates along an axis that coincides with the long axis of the coring assembly 110. Various mechanisms can be used to achieve such relative movement of the coring assembly components, some of which are described herein.

Figure 2:
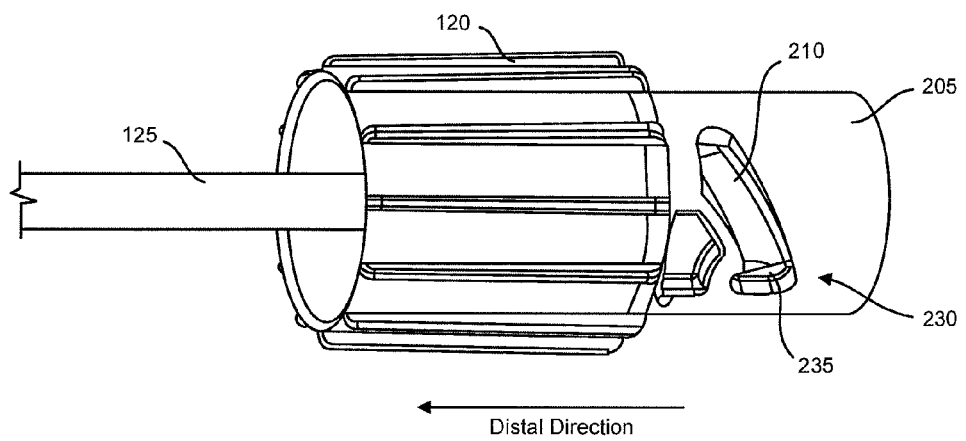
FIG. 2 shows an enlarged view of a second handle component and a portion of an outer cutting tube of the device.

FIG. 2 shows an enlarged view of the second handle component 120 and a portion of the outer cutting tube 125. FIG. 2 does not show the first handle component 115. The outer cutting tube 125 is attached to an interior region of the second handle component 120. The second handle component 120 has a tubular coupling region 205 that rotatably fits within the first handle component 115. One or more inclined guide tracks 210 are positioned on the coupling region 205. The inclined guide track 210 slidably mates with a corresponding coupling component (such as one or more mating projections or pins, such as pin 505 shown in FIG. 5A) of the first handle component 115 when the components are coupled to one another. The guide track 210 can have a spiral or partial spiral shape that winds around the outer surface of the coupling region 205. As the first handle component 115 is rotated, it linearly translates along a pathway defined by the inclined guide track 210 via the mating projection sliding along the guide track 210. In this manner, the guide track 210 serves as a linkage that transforms the rotary motion of the first handle component 115 into corresponding linear motion along the long axis of the device, as described more fully below. In an embodiment, the outer cutting tube 125 and the inner tube 130 do not rotate relative to one another.

The guide track 210 can have one or more features that enable locking of the handle components 115, 120 into pre-determined states, such as open and closed states (described below). For example, at the proximal-most end 230 of the guide track 210, a seat or detent 235 can be located that locks the handle components 115, 120 relative to one another. Any quantity of detents 235 can be located along the length of the guide track 210 to removably lock the handle components 115, 120 in a variety of relative positions.

As mentioned, the guide track 210 in the second handle component 120 slidably mates with a mating projection in the first handle component 115 to form a force coupling therebetween. Rotation of the first handle component 115 relative to the second handle element 120 results in sliding movement of the projection within the guide track 210. The guide track 210 can have a detent feature 235, such as a seat or projection, that interferes with movement of the mating projection at the upper and lower ends of the track 210 to impart resistance to movement. In an embodiment, the resistance to movement induces a palpable and/or audible snap, as well as transitional lock in the open and closed states.

In an embodiment, the track 210 has a recess or seat on the lower surface of the proximal-most end 230 of the track 210. A compressive load (imparted with downward or distal-directed pressure on the proximal first handle component 115 during introduction of the bone harvester into the bone) causes the mating projection of the first handle component 115 to nest into the recess. This results in coupled rotational movement of the first (proximal) handle component 115 and the second (distal) handle component 120 when a distal-directed load is applied to the first handle component 115. Thus, the inner tube 130 and outer cutting tube 125 rotate in unison when both a distal-directed force and rotation is applied to the first handle component 115 (or the cap 122). The depth of the recess can be less than the diameter of the mating projection such that, when the distal-directed force is reduced and/or the resistance to rotation increases, the mating projection rides up over the recess and along the spiral tract. This terminates the coupled rotation between the first and second handle components 115, 120 and results in linear movement of the inner tube 130 relative to the outer cutting tube 125 such as toward a closed position. This permits the operator to rotate both the first and second handle components 115, 120 while applying distal pressure on the first handle component 115 or cap 122 while maintaining the device in an open state (described below). The operator can then relax the distal-directed force and rotate the first handle component 115 relative to the second handle component 120 to transition and/or lock the system in an open or closed state.

A similar but reverse oriented mechanism, such as a recess on the upper portion of the distal-most end of the guide track 210, can be used to lock the instrument in a closed position during withdrawal of the instrument. For example, when a proximal-directed force is applied to the first handle component 115, the mating projection of the first handle component 115 can nest into the recess of the distal-most end of the guide track 210 such that coupled rotational movement of the first (proximal) handle component 115 and the second (distal) handle component 120 is achieved.

Figure 3:
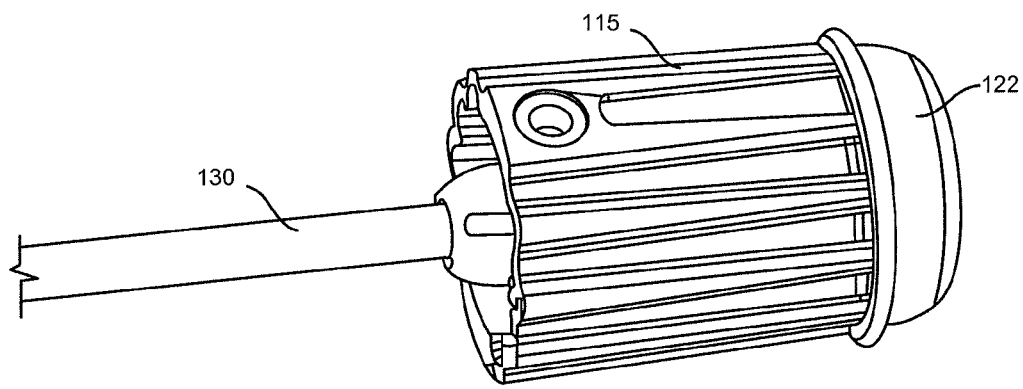
FIG. 3 shows an enlarged view of a first handle component and a portion of the inner tube of the device.
Figure 4:
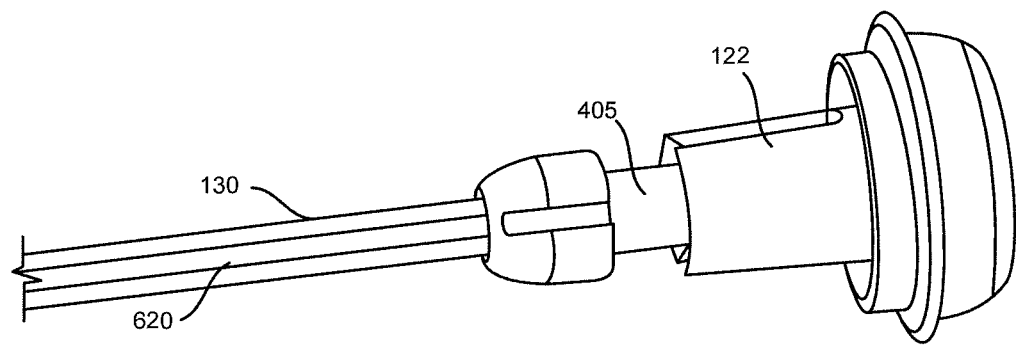
FIG. 4 shows the inner tube and a cap.

FIG. 3 shows an enlarged view of the first handle component 115 and a portion of the inner tube 130. For clarity of illustration, FIG. 3 does not show the second handle component 120. As mentioned, the first handle component 115 is positioned adjacent a cap 122. The inner tube 130 extends through the first handle component 115 and attaches to the cap 122. This is described in more detail with reference to FIG. 4, which shows the inner tube 130 and the cap 122 without the first handle component 115. The inner tube 130 has a proximal coupler 405 that mates with a portion of the cap 122 such that the inner tube 130 is attached to the cap 122. Any movement of the cap 122 is translated into corresponding movement of the inner tube 130. Thus, linear or rotational movement of the cap 122 translates to corresponding linear or rotational movement of the inner tube 130.

Figure 5A:
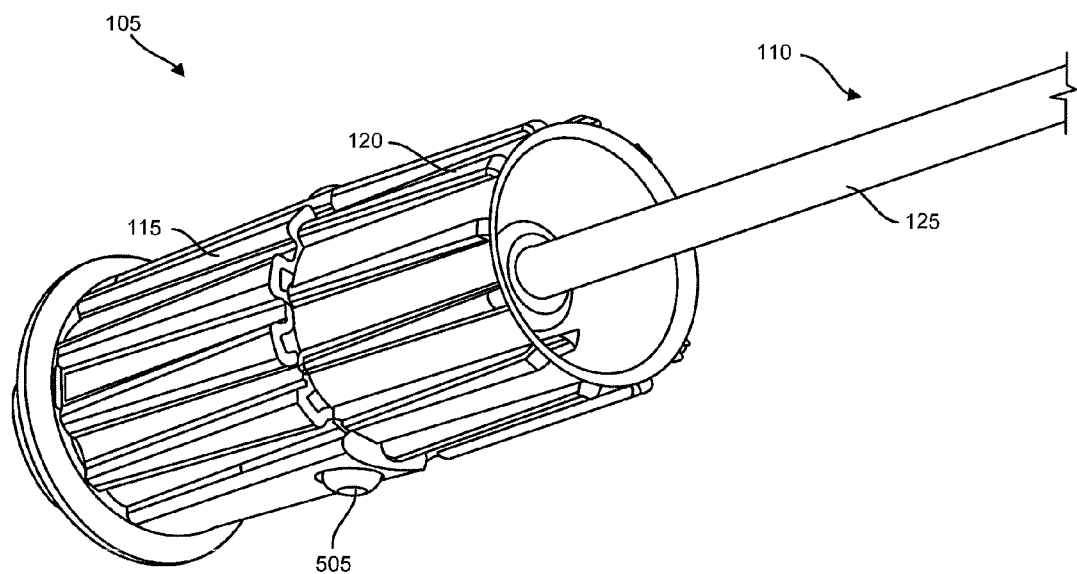
FIG. 5A shows a perspective view of the handle and a portion of the coring assembly while the device is in a "closed" state.
Figure 5B:
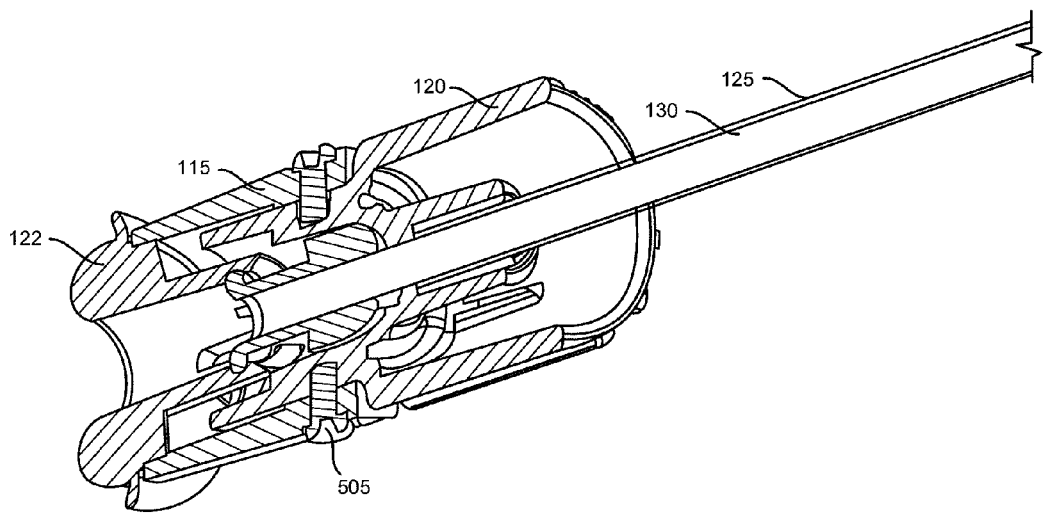
FIG. 5B shows a cross-sectional view of the device while in the closed state.

An exemplary manner in which linear translation of the inner tube 130 is achieved is now described with reference to FIGS. 5A-5D. FIG. 5A shows a perspective view of the handle 105 and a portion of the coring assembly 110 while the device is in a "closed" state. FIG. 5B shows a cross-sectional view of the device while in the closed state. In the closed state, the first handle component 115 is positioned immediately adjacent the second handle component 120, which means that the distal edge of the inner tube 130 is positioned at or distally of the distal edge of the outer cutting tube 125. In other words, the inner tube 130 is extended distally relative to the outer cutting tube 125 when the device is in the "closed" state, as described more fully below.

A pair of pins 505 or another coupling structure extend through the first handle component 115 and into the guide tracks 210 (FIG. 2) in the second handle component 120. When the device is in the closed state, the pins 505 are located at the proximal-most location of the inclined guide tracks 210. As mentioned, the guide track 210 can have one or more detents 235 that lock the device in the closed state or the open state. As mentioned, the outer cutting tube 125 is attached to the second handle component 120, while the inner tube 130 is attached to the cap 122 via the proximal coupler 405.

Figure 5C:
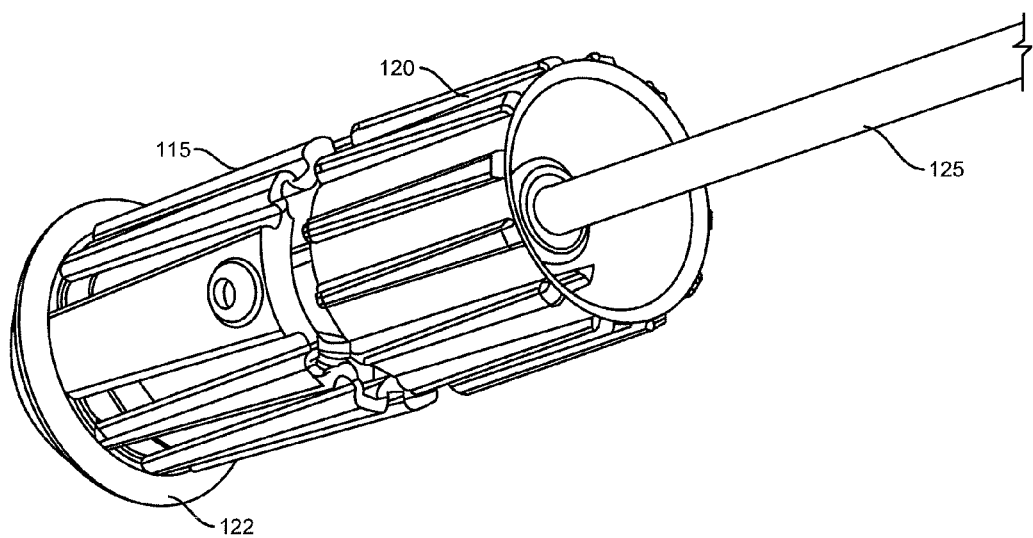
FIG. 5C shows the device in an "open" state that is achieved by rotating the first handle component relative to the second handle component.
Figure 5D:
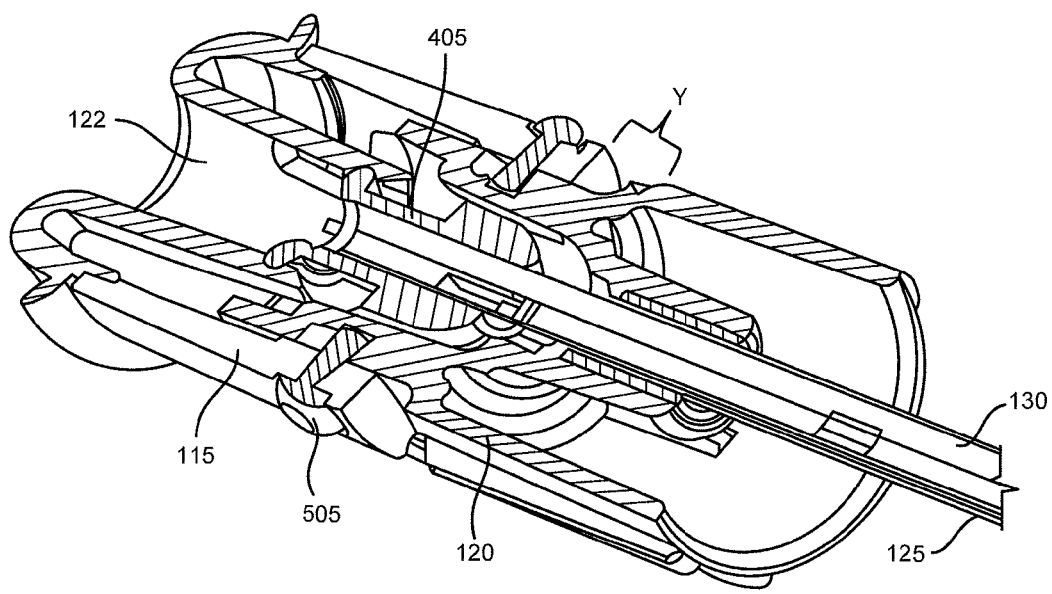
FIG. 5D shows a cross-sectional view of the device while in the open state.

FIG. 5C shows the device in an "open" state that is achieved by rotating the first handle component 115 relative to the second handle component 120. FIG. 5D shows a cross-sectional view of the device while in the open state. In an embodiment, the device transitions to the open state from the closed state by rotating the first handle component 115 about a 90 degree rotation. It should be appreciated, however, that various amounts of rotation can achieve the transition from a closed to an open state, and vice versa.

As mentioned, rotation of the first handle component 115 relative to the second handle component 120 results in linear translation of the inner tube 130 in a proximal direction relative to the outer cutting tube 125. Thus, in the open state, the distal edge of the inner tube 130 is positioned proximal of the distal edge of the outer cutting tube 125. In other words, the inner-most region of the inner tube 130 is retracted into the outer cutting tube 125 when the device is in the open state. When in the open state, the device can harvest a sample of tissue, as described more fully below. The linear translation is the result of the linkage (via the guide track 210) between the first handle component 115 and the second handle component 120 via the inclined guide track 210 (FIG. 2). Note that in the second state, the first handle component 115 is spaced from the second handle component 120 by a distance Y (FIG. 5D) as a result of the linear translation. The linear translation along the distance Y has also caused the cap 122 to linearly translate along the distance Y. Because the cap 122 is attached to the inner tube 130 (via the coupler 405), the inner tube 130 also linearly translates relative to the outer cutting tube 125, which is attached to the second handle component 120. In this manner, linear translation of the inner tube 130 relative to the outer cutting tube 125 is achieved. It should be appreciated that other mechanisms can be used.

Figure 6:
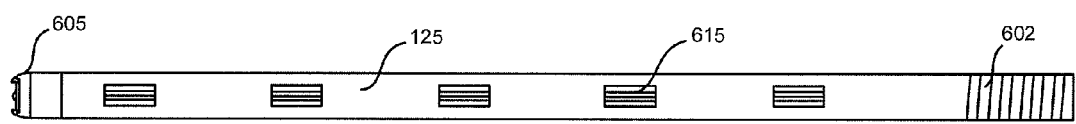
FIG. 6 shows a side view of the outer cutting tube.

The configurations of the outer cutting tube 125 and the inner tube 130 are now described in more detail. FIG. 6 shows a side view of the outer cutting tube 125, which is tubular in shape with an internal shaft that runs the length of the outer cutting tube 125. As mentioned, a proximal region 602 of the outer cutting tube 125 attaches to the second handle component 120 in the assembled device. A series of fenestrations 615 are positioned along the length of the outer cutting tube 125. The fenestrations 615 essentially provide windows into the internal shaft of the outer cutting tube 125 that can assist in viewing of the contents of the tubes, as described below.

Figure 7:
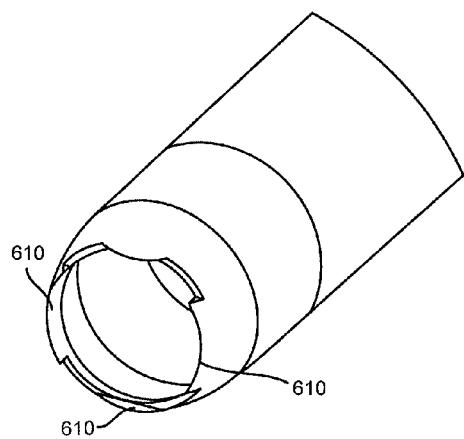
FIG. 7 shows an enlarged view of a distal region of the outer cutting tube.

A distal edge 605 of the outer cutting tube 125 is adapted for cutting or otherwise penetrating through the material being cored, such as through bone. In this regard, the distal edge 605 can be sharpened. FIG. 7 shows an enlarged view of an exemplary embodiment of the distal region 605 of the outer cutting tube 125. A series of teeth 610 are positioned at the distal end 605 of the outer cutting tube 125. The teeth 610 can be arranged in a saw-tooth pattern or in a castellated pattern to grind or micro-fracture cancellous bone via an oscillating or rotational application. The distal teeth 610 can have a raked configuration to reduce potential for bone collecting between the teeth, which could potentially make the teeth less effective in cutting through the bone.

Figure 8:
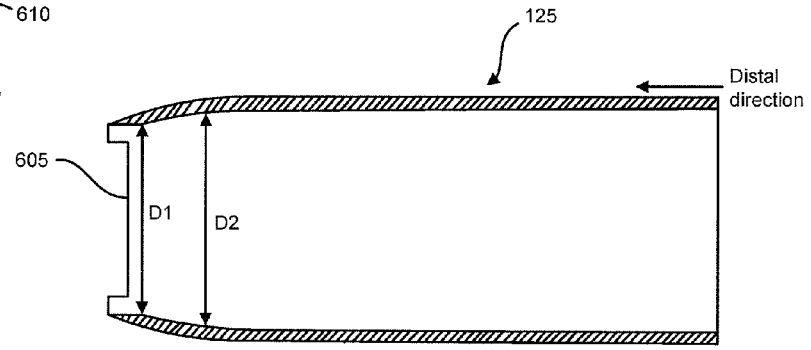
FIG. 8 shows a cross-sectional view of the distal region of the outer cutting tube.

FIG. 8 shows a cross-sectional view of the distal region 605 of the outer cutting tube 125. The external wall of the outer cutting tube 125 is tapered such that the outer diameter gradually decreases moving in the distal direction. The distal taper can reduce potential for penetrating cortical walls of bone with glancing contact during use of the device, as described below. Proximal of the distal edge 605, the internal diameter of the outer cutting tube 125 has an internal taper that decreases from D2 to D1 moving toward the distal edge 605.

With reference again to FIG. 4, the inner tube 130 is an elongated tube that is sized to fit concentrically within the internal shaft of the outer cutting tube 125. An elongated slot 620 extends along the entire length or along a portion of the length of the inner tube 130. The slot 620 is aligned with the fenestrations 615 of the outer cutting tube 125 in the assembled device to assist in viewing of the contents of the tubes.

Figure 9:
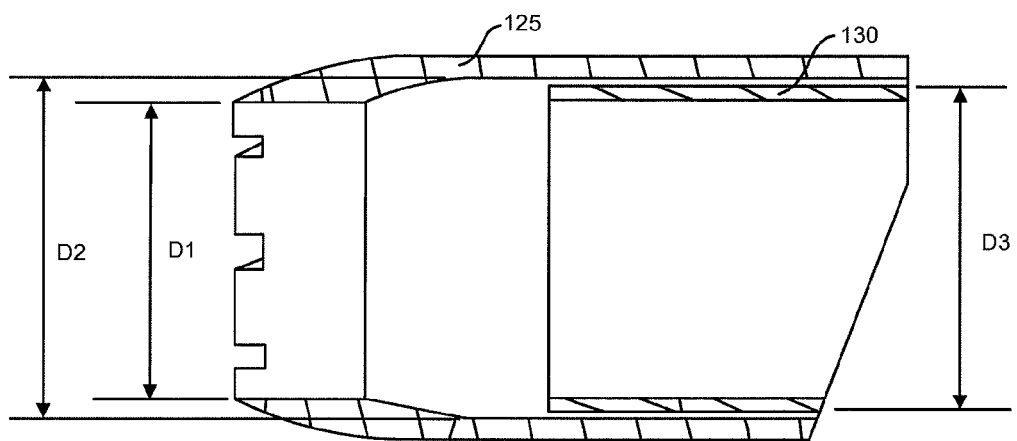
FIG. 9 shows a cross-sectional view of the distal region of the coring assembly with the inner tube positioned within the outer cutting tube.

FIG. 9 shows a cross-sectional view of the distal region of the coring assembly 110 with the inner tube 130 positioned within the outer cutting tube 125. With the device in the "open" state shown in FIG. 9, the distal edge of the inner tube 130 is located proximal to the internal taper of the outer cutting tube 125. The inner tube 130 has an external diameter D3 that is smaller than the diameter D2 (at the beginning of the taper) but larger than diameter D1 (at the end of the taper). When relative movement between the inner tube 130 and the outer cutting tube 125 occurs, the distal edge of the inner tube 130 moves toward the distal edge of the outer cutting tube 125 (or vice-versa) such that the device moves to a "closed" state. When in the closed state, the internal taper of the outer cutting tube 125 interferes with the outer diameter of the inner tube 130 to cause the inner tube 130 to reduce in diameter at a distal region of the inner tube 130. The slot 620 facilitates such reduction in diameter. The reduction in diameter creates a compressive force on a sample that is present in the inner tube 130, as described more fully below.

An exemplary use of the device is now described. The device is first placed in the "open" state such that the inner tube 130 is retracted into the outer tube 125, as was shown in FIG. 8. As discussed above, the device can be placed in the open state by actuating the handle 105, such as by rotating the first handle component 115 relative to the second handle component 120. The use of the device is described in the context of the removal of bone material from a patient during a surgical procedure. For example, the device can be used within or in the region of a person's vertebral bones. In an embodiment, the device is used to obtain core samples from the ilium of the pelvis, such as in the region of the iliac crest. The device can be used in other regions of the vertebra. The device can also be used in osseous and osseous cartilaginous regions of the body, as well as other locations of the body.

A pathway can first be formed through the cortical bone using a separate device. The physician inserts the distal end of the coring assembly 110 through the pathway and into the cancellous bone. The tapered outer walls of the outer cutting tube reduce the potential for penetrating cortical walls of bone with glancing contact. A physician grasps the device by the handle 105 and applies a forward pressure of the distal edge 605 of the outer tube 125 against the cancellous bone. The physician can impart a rotational oscillation to the distal edge 605 by rotating the handle 105. As mentioned, the handle 105 can be configured to lock into the open position so that the device does not inadvertently transition to the closed position during this step. The oscillating rotation of the device effects micro-fracturing of the cancellous trabeculae. The sharpened distal edge 125 of the outer tube 125 and the teeth 610 facilitate such micro-fracturing. In this manner, a distal region of the coring assembly 110 penetrates into the cancellous bone. A plug of cancellous bone is now positioned within the distal region of the coring assembly 110 as a result of the coring assembly's penetration into the bone. That is, a plug or piece of cancellous bone that substantially conforms to the inner shape of the coring assembly is positioned within the inner tube 130. The piece can have various shapes.

After a desired depth of cancellous penetration is achieved, the physician can stabilize the second handle portion 120 with a first hand handle with one hand. Any portion of the coring assembly 110, such as the outer cutting tube 125, can have one or more indicia to assist in identifying the depth of penetration. The physician then rotates the first handle portion 115 with the other hand to cause the device to transition to the "closed state." In an embodiment, an audible and/or tactile detent 235 can be associated with the device being moved to a fully closed position. As discussed above, when the device moves to the closed state, the distal edge of the inner tube 130 moves toward the distal edge of the outer cutting tube 125. The internal taper of the outer cutting tube 125 interferes with the outer diameter of the inner tube 130 to cause the inner tube 130 to reduce in diameter at a distal region of the inner tube 130. The reduction in diameter creates a compressive force on the sample of cancellous bone that is present in the inner tube 130.

The compressive force secures or stabilizes the cored cancellous bone. The instrument is then rotated and/or tensioned to shear the bone at the terminus of the instrument. The device is subsequently withdrawn from the bone while the bone sample remains within the inner tube 130. The withdraw of the device from the bone can be performed with or without continued rotation of the handle 105.

As mentioned, the outer cutting tube 125 has fenestrations 615 that align with a slot 620 in the inner tube 130. The cancellous bone accumulated within the inner tube 130 (which can be one or more plugs of bone) can be observed through the fenestrations 615 and the slot 620. It should be appreciated that the procedure can be performed multiple times to collect a plurality of samples within the inner tube 130 wherein the samples are positioned in sequence within the inner tube 130. The operator can visually verify the quantity of samples within the inner tube by looking through the fenestrations in the outer tube.

Figure 10:
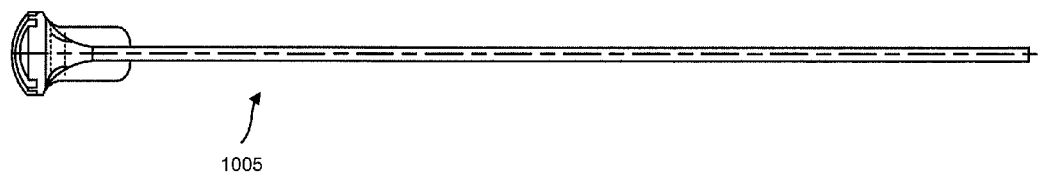
FIG. 10 shows a side view of a tamping member that interfaces with the core sample device.

Once the samples are filled to the capacity of the inner tube 130, the samples can be extracted. In an embodiment, this is accomplished by using a tamping member 1005 that interfaces with the core sample device (see FIG. 10). The core sample device is first moved to the open state. The tamping member 1005 comprises an elongated, rod-like plunger that fits into a longitudinal bore or cannula that runs the entire length of the core sample device (through the handle 105 and the coring assembly 110). The tamping member 1005 is inserted into the longitudinal bore (such as through a hole at the proximal end of the handle 105) to push the bone sample (s) out of the inner tube 130. In this manner, the samples are ejected from the coring assembly 110.

Although embodiments of various methods and devices are described herein in detail with reference to certain versions, it should be appreciated that other versions, embodiments, methods of use, and combinations thereof are also possible. Therefore the spirit and scope of the devices and methods described herein should not be limited to the description of the embodiments contained herein.

The invention claimed is:

1. A bone coring device, comprising:
a handle including a first handle component and a second handle component, the first handle component being rotatably coupled to the second handle component, and wherein the second handle component includes a tubular coupling region that rotatably fits within the first handle component, the coupling region having a linkage feature that slidably mates with a corresponding coupling component of the first handle component;
a coring assembly mechanically coupled to the handle, the coring assembly including:
(a) an elongated outer cutting member attached to the second handle component and having an internal bore and distal edge adapted to cut through cancellous bone;
(b) an elongated inner member attached to a cap that is positioned adjacent a proximal end of the first handle component, the elongated inner member being slidably positioned within the internal bore of the outer cutting member;
wherein rotatable movement of the first handle component relative to the second handle component and interaction of the linkage feature with the coupling component causes relative, linear movement between the first handle component and the second handle component, which results in the elongate inner member and the elongate outer cutting member not rotating relative to one another, as well as linear movement of the elongated inner member relative to the elongated outer cutting member to facilitate coring of a sample of bone when the coring assembly is positioned within the bone.

2. A device as in claim 1, wherein rotatable movement of the first handle component causes the coring assembly to transition between an open state and a closed state, wherein (a) in the open state, a distal-most region of the inner member is completely retracted within the outer cutting member; and (b) in the closed state, the distal-most region of the inner member is radially compressed within a tapered region of the outer cutting member.

3. A device as in claim 1, further comprising a detent structure, wherein the detent can be engaged to couple rotational movement of the first handle component to rotational movement of the second handle component such that the second handle component rotationally moves with the first handle component, and wherein the detent is engaged solely by relative movement between the first handle component and the second handle component.

4. A device as in claim 3, wherein the detent is engaged by application of a distally directed load onto the first handle component.

5. A device as in claim 4, wherein the detent disengages by removal of the distally directed load in rotational movement between the first handle component and the second handle component.

6. A device as in claim 3, wherein the detent structure comprises a protrusion on one of the first handle component and the second handle component and a guide track on the other of the first handle component and the second handle component, wherein the protrusion slidably mates with the guide track.

7. A device as in claim 1, wherein the distal edge of the outer cutting member has teeth that facilitate cutting of cancellous bone.

8. A device as in claim 7, wherein the teeth are raked.

9. A device as in claim 1, wherein the outer cutting member has a distal region with outer walls that are tapered such that a diameter of the outer cutting member reduces moving in a distal direction along the outer cutting member.

10. A device as in claim 1, wherein the outer cutting member has a plurality of fenestrations positioned along a longitudinal length of the outer cutting member, and wherein the inner member has an elongate slot extending along a longitudinal length of the inner member, wherein the fenestrations are aligned with the elongate slot at least during rotation of the first handle relative to the second handle.

11. A device as in claim 1, wherein an internal wall of a distal region of the outer cutting member is tapered such that the inner member undergoes a decrease in diameter.

12. A device as in claim 1, wherein a longitudinal bore extends through the entire device, and further comprising a tamping member that fits into the bore of the entire device, the tamping member adapted to expel a sample positioned within the coring assembly.

13. A device as in claim 1, wherein the first handle component is positioned proximal of the second handle component.

14. A device as in claim 1, wherein the linkage feature is an inclined guide track that defines the linear movement of the first handle component relative to the second handle component.

15. A device as in claim 1, further comprising at least one indicia on the outer cutting member that can be used to indicate a penetration depth of the outer cutting member into tissue.

16. A bone coring device, comprising
a handle assembly having a proximal handle component and distal handle component joined relative to each other with a spiral tract mechanism that links relative rotational movement with longitudinal movement, wherein the proximal handle component and the distal handle component are rotationally movable relative to one another about an axis and translationally movable relative to one another along the axis;

a tubular assembly distally attached to the handle assembly, the tubular assembly including an outer cutting tube having a distal taper, and a slotted tube within the outer cutting tube;

wherein longitudinal movement of the proximal handle component relative to the distal handle component causes longitudinal translation of the slotted tube relative to the outer cutting tube, and wherein rotationally advancing the proximal handle component relative to the distal handle component results in annular constriction of a distal region of the slotted tube within the distal taper of the outer cutting tube.

17. A device as in claim 16, further comprising a detent structure associated with the spiral tract mechanism, wherein the detent structure provides threshold limited resistance to relative rotational movement of the proximal handle component relative to the distal handle component.

18. A device as in claim 16, wherein the detent structure includes a guide track that slidably mates with a protrusion to guide and limit relative movement between the proximal handle component and the distal handle component.

19. A device as in claim 16, wherein the outer cutting tube with the distal taper is translationally and rotationally fixed to the distal handle component.

* * * * *